United States Patent [19]

Scott

[11] Patent Number: 4,896,660
[45] Date of Patent: Jan. 30, 1990

[54] ARM ELEVATOR SUPPORT DEVICE

[76] Inventor: James W. Scott, P.O. Box 7630, Tifton, Ga. 31794

[21] Appl. No.: 245,344

[22] Filed: Sep. 16, 1988

[51] Int. Cl.$^4$ .............................................. A61F 5/00
[52] U.S. Cl. ...................................... 128/77; 128/78; 128/94
[58] Field of Search ................ 128/77, 78, 165, 80 R, 128/94

[56]  References Cited

U.S. PATENT DOCUMENTS

| | | |
|---|---|---|
| 195,941 | 10/1877 | McCabe . |
| D. 287,641 | 1/1987 | Schaefer . |
| 1,257,297 | 2/1918 | Brown .................................. 128/88 |
| 1,295,297 | 2/1919 | French ................................. 128/88 |
| 1,466,487 | 8/1923 | Shaffer ................................ 128/88 |
| 1,639,815 | 8/1927 | Siebrandt ............................. 128/88 |
| 1,768,770 | 7/1930 | Kettelkamp ......................... 128/88 |
| 1,808,422 | 6/1931 | MacDonald . |
| 2,594,809 | 4/1952 | Sanders . |
| 2,744,526 | 5/1956 | Saylors . |
| 3,215,138 | 11/1965 | Groesbeck . |
| 4,180,870 | 1/1980 | Radulovic et al. ................... 128/77 |
| 4,210,317 | 7/1980 | Spau et al. . |
| 4,370,976 | 2/1983 | Wanchik et al. . |
| 4,373,517 | 2/1983 | Criscuolo ............................. 128/77 |
| 4,375,809 | 3/1983 | Meals . |
| 4,489,716 | 12/1984 | Blackwood et al. . |
| 4,559,932 | 12/1985 | Salort .................................. 128/77 |
| 4,564,008 | 1/1986 | Donaloo . |
| 4,651,719 | 3/1987 | Funk et al. .......................... 128/77 |
| 4,669,451 | 6/1987 | Blauth et al. ....................... 128/78 |
| 4,784,128 | 11/1988 | Scheuermann ..................... 128/77 |

FOREIGN PATENT DOCUMENTS

| | | | |
|---|---|---|---|
| 102396 | 11/1937 | Australia ............................. 128/87 |
| 3517343 | 11/1986 | Fed. Rep. of Germany ........ 128/77 |
| 20530 | 8/1918 | France ................................. 128/77 |
| 2589722 | 5/1987 | France ................................. 128/78 |

OTHER PUBLICATIONS

"Better Sleep" Arm Cushion, 5/436.

Primary Examiner—William Pieprz
Assistant Examiner—Huong Q. Pham
Attorney, Agent, or Firm—Bradford E. Kile

[57]  ABSTRACT

The invention relates to an arm elevation support device comprising a generally monolithic humerus support, a contoured well shoulder anchor, and a radius and ulna support. The monolithic humerus support is operable to abut against a patient's side and underlies the humeral portion of a patient's arm. The contoured well shoulder anchor includes a contoured sleeve portion operable to be worn around the acromial portion of a patient's well arm and two straps which releasably connect the well shoulder anchor to the monolithic humerus support. The radius and ulna support connects to the monolithic structure and provides support for a patient's forearm and hand.

21 Claims, 3 Drawing Sheets

ARM ELEVATOR SUPPORT DEVICE

BACKGROUND OF THE INVENTION

This invention relates to a novel arm elevation support device for use following an orthopedic procedure. More specifically, this invention relates to an arm elevation device for recuperative support following rotator cuff surgery, humeral head or shaft fracture correction, or the like.

Following an operation or arm injury to a shoulder, elbow, or hand it is often necessary to immobilize the afflicted arm in a substantially stationary, elevated position. In the past, a metallic arm support structure has been used in conjunction with a plaster cast to immobilize a recuperating arm. A lack of patient mobility is a necessary consequence of such an arrangement due to the rigidity of the metal frame member. Moreover, the weight of the overall apparatus adds an imbalance factor that is cumbersome to a patient.

In other instances, prior arm support structures have been developed which, while extending the humerus away from a patient's upper torso, require the elbow to bend at such a degree that the forearm and wrist extend in a direction back across the patient's chest. This high degree of bending restricts circulation in the arm and can result in an accumulation of interstitial fluid in the tissue, clinically known as edema, or other related complications.

Further, depending on the patient's condition, it may be desirable to support the wrist and to allow active hand therapy. Past arm support structures have not provided adequate wrist support or allowed for active hand therapy, thereby raising the risk of various complications to the hand and wrist.

Still further, some past arm elevation supports have included a pair of straps, one of which extends from the front side of the support and around the patient's neck to the rear of the support, and the other of which extends around the waist of the patient. This arrangement tends to impart stress to a patient's neck and has been shown to cause discomfort and exhaustion. In addition, this arrangement has also been shown to cause substantial discomfort to the patient when shifting from an erect to a supine position.

The difficulties suggested in the preceding are not intended to be exhaustive, but rather are among many which may tend to reduce the effectiveness and patient satisfaction with prior arm elevation support devices. Other noteworthy problems may also exist; however, those presented above should be sufficient to demonstrate that arm elevation supports appearing in the past will admit to worthwhile improvement.

OBJECTS AND BRIEF SUMMARY OF THE INVENTION

Objects

It is therefore a general object of the invention to provide a novel arm elevation support device which will obviate or minimize difficulties of the type previously described.

It is a specific object of the invention to provide an arm elevation support device which may be used to facilely abduct an arm following rotator cuff surgery or shoulder fracture correction.

It is another object of the invention to provide an arm elevation support device which reduces pressure on the neck by distributing the weight of the recuperating arm evenly over the well shoulder and upper torso of a patient.

It is still another object of the invention to provide an arm elevation support device which minimizes the tendency for edema to occur in a recuperating arm.

It is a further object of the invention to provide an arm elevation device which allows the patient to shift easily between erect and supine positions.

It is yet a further object of the invention to provide an arm elevation support device which will support the skeleton of the hand as well as the radius and ulna of the arm.

It is still a further object of the invention to provide an arm elevation support device which synergistically provides active hand therapy and allows access to the hand for neurovascular inspection.

It is yet another object of the invention to provide an arm elevation support device which is easily manipulated to provide varying degrees of elevation of the radius and ulna of the arm following corrective surgical procedures.

It is additionally an object of the invention to provide an arm elevation support device which is not required to be used in combination with a plaster cast or metallic support apparatus.

It is yet still a further object of the invention to provide an arm elevation support device which will effect any combination of the foregoing objects.

BRIEF SUMMARY OF A PREFERRED EMBODIMENT OF THE INVENTION

A preferred embodiment of the invention which is intended to accomplish at least some of the foregoing objects includes a generally monolithic humerus support having a first proximal surface to abut against a patient's side; a second surface underlying and supporting the humeral portion of a patient's arm; a third distal surface substantially parallel, in operation, to the first proximal surface; and a fourth surface substantially normal to the first proximal surface. A contoured well shoulder anchor includes a contoured sleeve portion operable to be worn around an acromial region of a patient's arm and first and second straps which extend across a patient's upper body and releasably connect onto a front and back surface respectively of the monolithic humerus support. A radius and ulna support is releasably connected to the third distal surface and may be operably positioned at selective angles to selectively elevate a patient's forearm and hand.

THE DRAWINGS

Other objects and advantages of the present invention will become apparent from the following detailed description of a preferred embodiment thereof taken in conjunction with the accompanying drawings, wherein.

DETAILED DESCRIPTION

Figure 1:
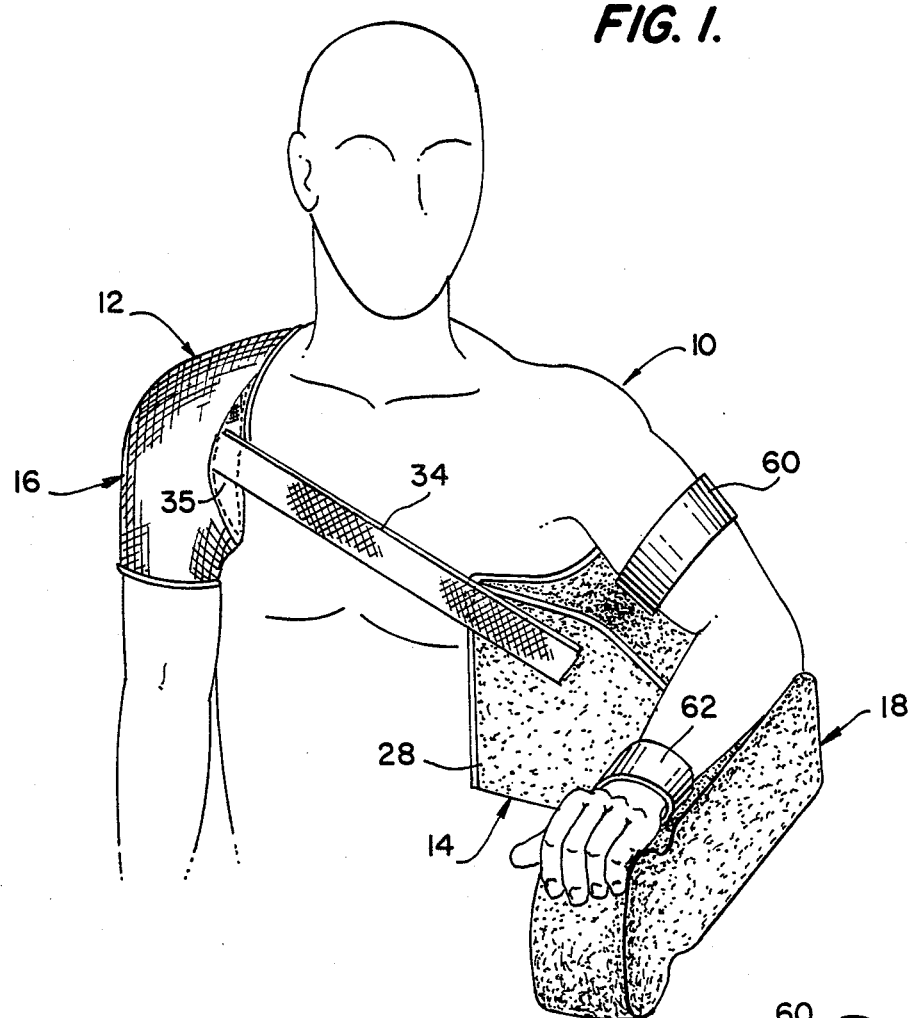
FIG. 1 is an axonometric view disclosing the context of the subject invention and depicts a patient wearing a shoulder sleeve anchor which supports an arm elevation device positioned to abduct a patient's left operative shoulder at approximately a forty-five degree angle in accordance with a preferred embodiment of the invention.

Referring now to the drawings, wherein like numerals indicate like parts, and initially to FIG. 1, there will be seen an operative context of the subject invention. More particularly, a patient 10 is shown following rotator cuff surgery, humeral head or shaft fracture correction, or the like, wearing an arm elevation support device 12 in accordance with a preferred embodiment of the invention. More specifically, the subject arm elevator support device 12 includes a generally monolithic humerus support 14, a contoured shoulder anchor 16, and a radius and ulna support 18.

Figure 2:
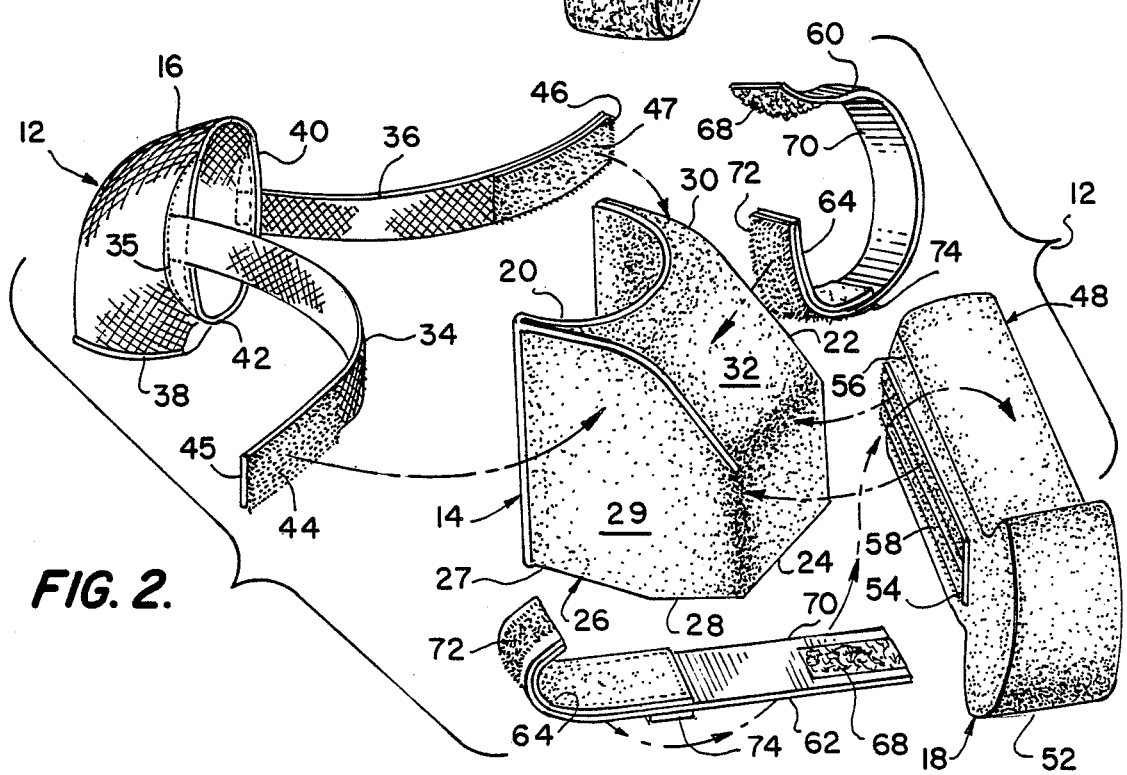
FIG. 2 is an exploded assembly view of the subject arm elevation support device which includes a well shoulder anchor, a monolithic humerus support, a radius and ulna support, a first humerus retaining strap, and a second radius and ulna retaining strap.

Referring specifically to FIG. 2 there will be seen an exploded view of the subject arm elevation support device 12. The generally monolithic humerus support 14 includes a first proximal surface 20 which is suitable to abut against a patient's side, note again FIG. 1. In this connection the first proximal surface 20 is longitudinally concave and generally conforms to a patient's lateral rib cage to distribute supporting loads of the subject arm elevation device 12. The monolithic humerus support 14 further includes a second surface 22 operable, in one preferred mode of the invention, for underlying and supporting the humeral portion of a patient's arm. This second surface 22 slopes at approximately a forty-five degree angle with respect to said first proximal surface 20 and abducts a patient's arm at approximately a corresponding forty-five degree angle with respect to an imaginary central longitudinal axis extending through the patient. The monolithic humerus support 14 further comprises a third distal surface 24 which is substantially planer and in an operating concept parallel to said first proximal surface 20. The distal surface 24 serves to cooperate with and support a radius and ulna support 18 in a manner which will be discussed in detail herein below. The monolithic humerus support 14 also includes a fourth surface 26 which extends between said first proximal surface 20 and said third distal surface 24 and in one embodiment of the invention functions to abduct a patient's arm at approximately a seventy-five degree angle. In this connection the fourth surface 26 includes an area 27 extending normal to said first proximal surface 20 and a sloping area 28 which is angled at approximately seventy-five degrees with respect to an imaginary axis of a patient's body and said distal surface 24.

The generally monolithic humerus support 14 is further bounded by a first lateral wall 29 and an opposed second lateral wall 30 to define in cooperation with the previously discussed surfaces a generally solid support structure. The monolithic humerus support 14 is preferably fabricated from an open cell polymeric foam which is light in weight, easily molded, and later sculptured into a desired configuration as discussed above. Moreover, the open cell foam structure is selected from a polymeric composition so as to provide a useful degree of compressive support when utilized in the manner discussed in this application.

The second surface 22, third distal surface 24, fourth surface 26, and first and second lateral walls 29 and 30 are covered with a pile cloth 32 of a design suitable to cooperate with hook type fastening strips to releasably provide a connection between two members. One brand of this type of fastening combination is known as VELCRO.

The contoured well shoulder anchor 12, as viewed in FIGS. 1 and 2, comprises a contoured sleeve portion 16 operable to be worn around the acromial region of a patient's well arm including a deltoideus and deltoid region of a patient's well shoulder, a first strap 34, and a second strap 36. The first strap 34 has a splayed end portion 35 and is connected to an anterior segment 38 of the contoured sleeve portion 16 and extends across a patient's upper torso to releasably connect to a lateral wall 29 of said monolithic humerus support 14. The second strap 36 has a similar splayed end portion 37 and is connected to a posterior segment 40 of the contoured sleeve portion 16 and extends across a back portion of a patient's upper torso to releasably connect to an opposed lateral wall 30 of said monolithic humerus support 14.

The contoured sleeve portion 16 is composed of an open weave cloth and includes an elastic underarm portion 42 which conforms to a patient's underarm to conform said contoured well shoulder anchor 12 to an acromial portion of a patient's arm. The straps 34 and 36 are also composed of an open weave cloth and additionally have hook type fastening patches 44 and 46 located on the free ends 45 and 47 of the straps 34 and 36 to releasably attached the straps 34 and 36 to said monolithic humerus support 14.

Still referring to FIG. 2, the radius and ulna support 18 comprises a generally monolithic member 48 having a solid rectangular shape and an enlarged end portion 49 configured to form a pair of hand-receiving members 50 and 52. A substantially rigid backing member 54 is longitudinally mounted on the radius and ulna support 18 and carries two substantially parallel hook type fastening strips 56 and 58 which securely affix said radius and ulna support 18 to the third distal surface 24 of said monolithic humerus support 14.

The radius and ulna support 18 is covered with pile cloth as discussed previously in connection with said monolithic humerus support 14.

Also seen in FIG. 2, a first retaining strap 60 is releasably connected to said monolithic humerus support 14 and circumferentially around wraps the humerus region of a patient's arm to provide retaining stability. A second retaining strap 62 is releasably connected to said radius and ulna support 18 and circumferentially wraps around the forearm of a patient. The retaining straps 60 and 62 are composed of an elastic material. A spongy cushioning material 64 is sewn to an inner side of a first half 66 of said retaining straps 60 and 62. A pile type fastening patch 68 is mounted on a second half 70 of each of said retaining straps 60 and 62 to engage a loop type fastening patch 72 mounted on the first half 66 of the retaining straps 60 and 62. A second hook type fastening patch 74 is mounted on said first half 66 to secure the retaining straps 60 and 62 to the designated monolithic humerus support 14 or radius and ulna support 18.

FIGS. 3-9, in cooperation with FIG. 1, disclose various techniques of abducting and/or recuperatively supporting a patient's arm utilizing the subject arm elevation support device 12. As previously discussed in FIG. 1, the arm elevation support device 12 may be fitted to a patient's left arm with the humerus extending at approximately a forty-five degree angle with respect to a central longitudinal axis of the patient's body. The patient's elbow is bent and the forearm and hand extend forward and substantially parallel to a ground surface.

Figure 3:
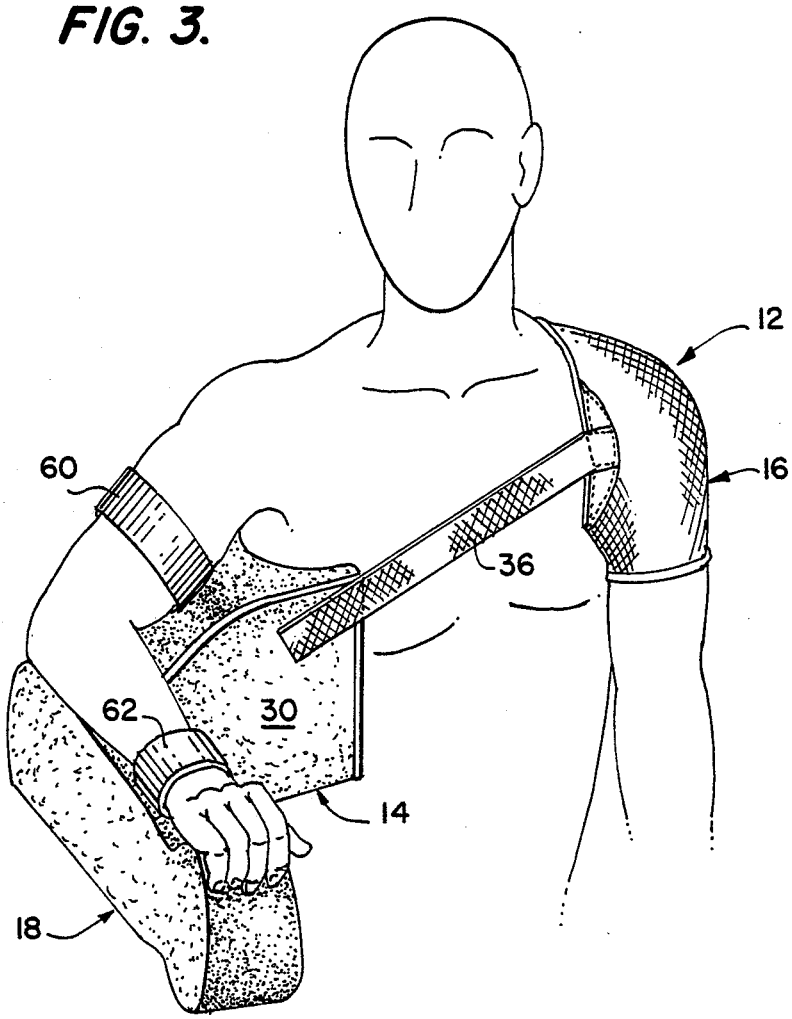
FIG. 3 is an axonometric view of an arm elevation support device as depicted in FIG. 1 wherein the subject support device is reversibly applied to support a patient's right arm at approximately a forty-five degree angle of abduction.

FIG. 3 discloses a view similar to FIG. 1 wherein a patient's right arm is the subject of recuperative support and the identical arm elevation support device 12, previously disclosed in connection with FIG. 1, is advantageously fitted to a patient by placing the monolithic humerus support 14 beneath the patient's right arm and retaining straps 60 and 62 releasably secure the arm to the monolithic humerus support 14 and radius and ulna support 18 respectively. The contoured well shoulder anchor 16 is fitted around the patient's left shoulder and straps 34 and 36 again extend across a patient's torso and are releasably connected to the lateral faces 29 and 30 of the monolithic humerus support 14.

Figure 4:
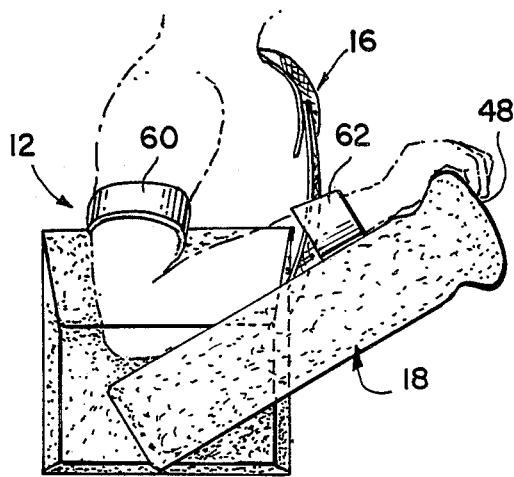
FIG. 4 is a side detail view of the subject invention showing the radius and ulna support affixed to the monolithic humerus support at an angle for elevating a patient's hand and wrist.
Figure 5:
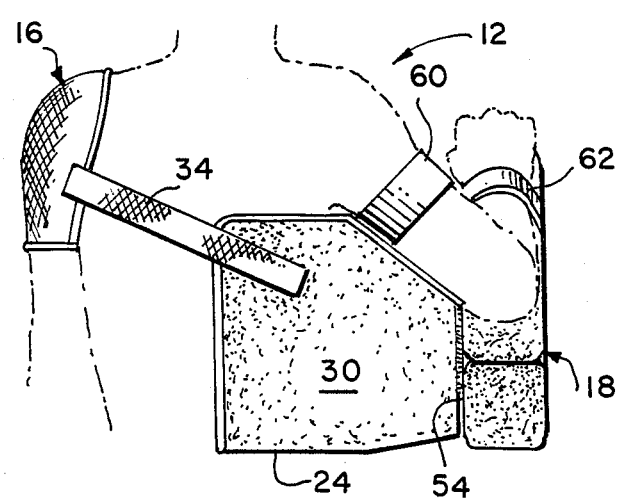
FIG. 5 is a back detail view of the subject arm elevation support device depicted in FIG. 4.

Referring specifically to FIGS. 4 and 5 it will be seen the arm elevation support device 12 fitted to a patient's right arm as discussed above wherein the radius and ulna support 18 is elevated at a distal end 48 by releasing the attachment of hook strips 56 and 58 to the distal pile surface 24 of the monolithic humerus support member 14 and reconnecting the radius and ulna support 18 at a desired angle of elevation through application of a normal force.

Figure 6:
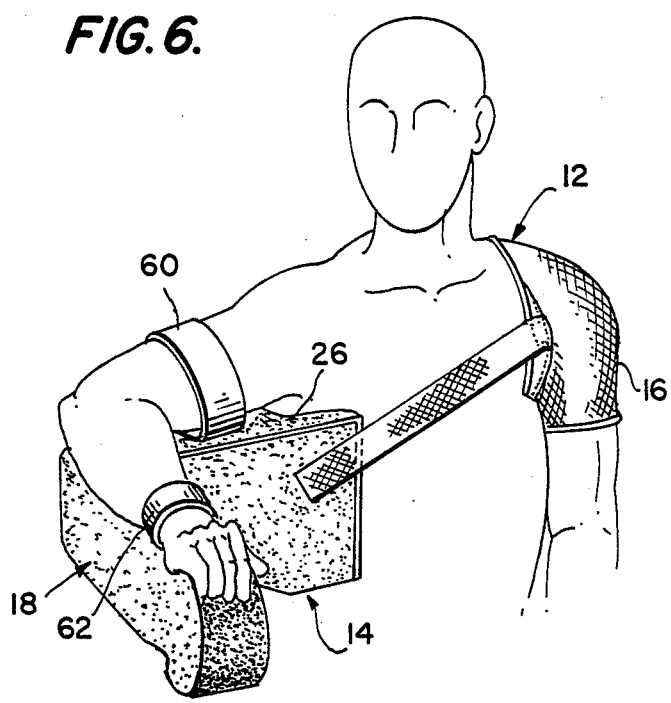
FIG. 6 is an axonometric view of the subject arm elevation support device used in an alternative preferred mode to abduct a patient's operative right arm at approximately a seventy-five to ninety degree angle.
Figure 7:
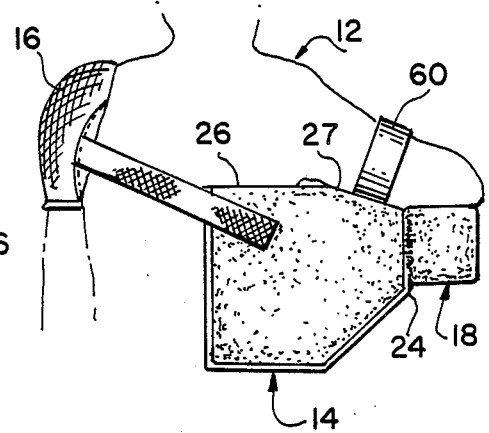
FIG. 7 is a back detail view of the subject arm elevation support device depicted in FIG. 6.
Figure 8:
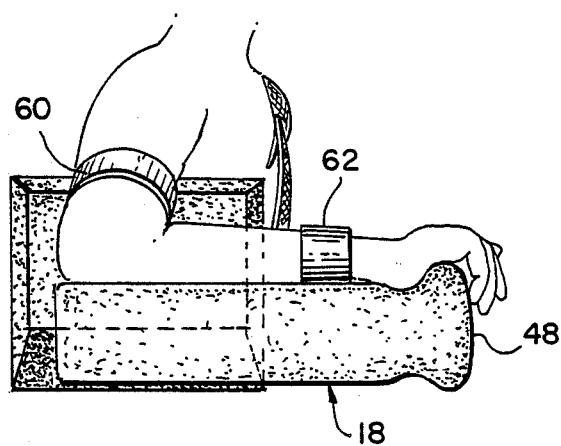
FIG. 8 is a side detail view of the subject arm elevation support device as depicted in FIG. 6.

Referring now to FIGS. 6–8, there is disclosed still a further advantageous mode of the subject arm elevation support device 12. In this mode of use the monolithic humerus support 14 is positioned beneath a patient's upper arm with the substantially normal surface 26 in an upward position and the segment sloping at approximately a seventy-five degree angle 27 underlies the humerus of a patient. The radius and ulna support 18 is again connected to the distal end 24 of the monolithic humerus support 14 and serves to support a patient's forearm in a substantially horizontal posture as shown specifically in FIG. 8.

Figure 9:
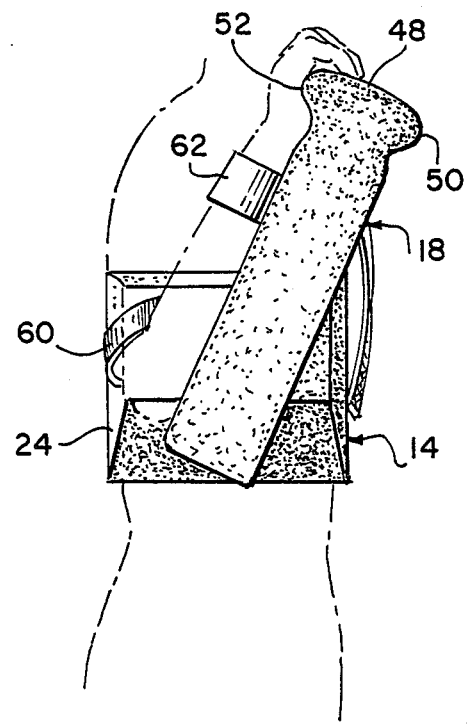
FIG. 9 is a side detail view of the subject invention showing a radius and ulna support positioned in a near-vertical elevated posture.

Turning now to FIG. 9, the subject arm elevation support device 12 is again fitted to support a patient's right arm; however, in this embodiment, the radius and ulna support 18 has been connected to the distal surface 24 of the monolithic humerus support 14 so as to carry a patient's hand in a substantially elevated posture. As previously discussed the end portion 49 includes a pair of hand-receiving members 50 and 52. A patient's hand operably extends around these members and by instituting a squeezing action a patient is able to induce blood circulation into the forearm and hand even though the forearm and upper arm of the patient are substantially immobilized by the subject arm elevation support device 12.

SUMMARY OF MAJOR ADVANTAGES OF THE INVENTION

After reading and understanding the foregoing description of the invention, in conjunction with the drawings, it will be appreciated that several distinct advantages of the subject arm elevation support device are obtained.

Without attempting to set forth all of the desirable features of the arm elevation support device at least some of the major advantages of the invention include the unique combination of a monolithic humerus support 14, a contoured well shoulder anchor 16, and a radius and ulna support 18 to facilely abduct an arm following rotator cuff surgery, humeral head or shaft fracture correction, or the like.

Additionally, the contoured well shoulder support 16 provides a means to evenly distribute the weight of the recuperating arm evenly over the well shoulder and upper torso of the patient while the contoured sleeve portion 38 acts to alleviate pressure on the patient's neck.

Still further the radius and ulna support 18 may be disconnected from the monolithic humerus support 14 and reattached at an elevating angle to minimize the tendency for edema to occur in a recuperating arm. Also, this feature allows a surgeon to modify the angled placement of the forearm during the recuperative stages of surgery.

While conventional arm abductors are cumbersome and may inhibit normal motor activity, the major members of the subject invention may be configured from a light in weight, easily moldable open cell polymeric foam allowing the patient to shift from an erect to a supine position while still providing the necessary stability to facilitate healing.

The radius and ulna support 18 includes an enlarged end portion 49 having hand-receiving members 50 and 52 which support the skeleton of the hand as well as the radius and ulna of a patient's arm.

In a similar vein, the hand-receiving members 50 and 52 are configured to function as an active hand therapy device wherein a patient squeezes the hand-receiving members to increase blood flow through the forearm. Also, the construction of the radius and ulna support 18 where the patient's forearm lies on top of the support 18 permits visual inspection of the patient's hand for neurovascular checks.

Still further the subject invention need not be used in conjunction with a plaster cast or metallic support apparatus since immobilization is created by the retaining straps 60 and 62 and by the releasably attachable feature of the hook and pile fastening strips 56 and 58 located on the radius and ulna support 18.

In describing the invention, reference has been made to preferred embodiments and illustrative advantages of the invention. Those skilled in the art, however, and familiar with the instant disclosure of the subject invention, may recognize additions, deletions, modification, substitutions and/or other changes which will fall within the purview of the subject invention and claims.

What is claimed is:

1. An arm elevation support device for recuperative support following rotator cuff surgery, humeral head or shaft fracture correction, or the like comprising:
    a generally monolithic humerus support having,
    a first proximal surface operable to abut against a patient's side, a second surface operable for underlying and supporting the humeral portion of a patient's recuperative arm, and a third distal surface substantially parallel in operation to said first proximal surface and extending at approximately a forty-five degree angle with respect to said second surface;

a contoured well shoulder anchor having, a contoured sleeve portion operable to be worn around the acromial region of a patient's well arm and shoulder and extend in supporting contact about the deltoideus and deltoid regions of a patient's well arm and shoulder, a first step connected to an anterior segment of said contoured well shoulder anchor, and extending across a patient's upper torso and being releasably connected to an anterior portion of said monolithic humerus support, and a second trap connected to a posterior segment of said contoured well shoulder anchor and extending across a back portion of a patient's torso and being releasably connected to a posterior portion of said monolithic humerus support wherein the shoulder region of a patient's opposing well arm operably provides support for said generally monolithic humerous support positioned on an opposite side of a patient's body for underlying and supporting the patient's recuperative arm; and a radius and ulna support releasably connected to said third distal surface of said monolithic humerus support for recuperatively supporting a hand and foreman of a patient.

2. An arm elevation support device as defined in claim 1 wherein:
said first proximal surface of said monolithic humerus support is concave to be operably received about a patient's lateral rib cage to laterally distribute supporting loads of said arm elevation support device.

3. An arm elevation support device as defined in claim 1 wherein:
said second surface of said monolithic humerus support extends at approximately a forty-five degree angle with respect to said first proximal surface of said monolithic humerus support.

4. An arm elevation support device as defined in claim 3 wherein said monolithic humerus support further comprises: a fourth surface being substantially normal to said first proximal surface of said monolithic humerus support.

5. An arm elevation support device as defined in claim 4 wherein:
said third distal surface of said monolithic humerus support extends at a substantially forty-five degree angle with respect to said second surface.

6. An arm elevation support device as defined in claim 1 wherein:
said monolithic humerus support is composed of polymeric foam.

7. An arm elevation support device as defined in claim 1 wherein:
said contoured well shoulder anchor is composed of an open weave cloth.

8. An arm elevation support device as defined in claim 1 wherein said contoured well shoulder anchor includes:
an elastic underarm portion which conforms to a patient's underarm to secure said contoured well shoulder anchor to the acromial portion of a patient's arm.

9. An arm elevation support device as defined in claim 1 wherein said radius and ulna support comprises:
a generally monolithic member having a solid rectangular shape.

10. An arm elevation support device as defined claim 9 wherein said radius and ulna support comprises:
an enlarged end portion with at least one hand-receiving member.

11. An arm elevation support device as defined in claim 10 wherein said radius and ulna support comprises:
an enlarged end portion having a pair of hand-receiving members.

12. An arm elevation support device as defined in claim 9 wherein said radius and ulna support comprises:
a substantially rigid, generally rectangular backing member affixed to a lateral face of said monolithic member and carrying at least one releasably connecting hook and pile type fastening strip.

13. An arm elevation support device as defined in claim 12 wherein said at least one hook and pile type fastening strip of said radius and ulna support comprises:
two substantially parallel, releasably connecting loop and pile type fastening strips.

14. An arm elevation support device as defined in claim 1 and further comprising:
a first retaining strap releasably connected to said monolithic support and being operable to extend about a humerus region of a patient's arm.

15. An arm elevation support device as defined in claim 14 and further comprising:
at least a second retaining strap releasably connected to said radius and ulna support and being operable to extend about the radius and ulna of a patient's arm.

16. An arm elevation support device for recuperative support following rotator cuff surgery, humeral head or shaft fracture correction, or the like comprising:
a generally monolithic humerus support having, a first, concave, proximal surface of said monolithic humerus support to be operably received about a patient's rib cage to laterally distribute supporting loads of said arm elevation support device, a second surface which extends at a substantially forty-five degree angle with respect to said first proximal surface of said monolithic humerus support, a third distal surface substantially parallel to said first proximal surface and extending at substantially a forty-five degree angle with respect to said second surface, and a fourth surface substantially normal to said first proximal surface of said monolithic humerus support and said third distal surface;

a contoured well shoulder anchor having, a contoured sleeve portion operable to be worn around the acromial region of a patient's well arm and shoulder and extend in supporting contact about the deltoideus and deltoid regions of a patient's well arm and shoulder, a first strap connected to an anterior segment of said contoured well shoulder anchor and extending across a patient's upper torso and being connected to an anterior portion of said monolithic humerus support, and a second strap connected to a posterior segment of said contour well shoulder anchor and extending across a back portion of a patients's torso and being releasably connected to a posterior portion of said monolithic humerus support wherein the shoulder region of a patient's opposing well arm operably provides support for said generally monolithic humerous support positioned on an opposite side of a patient's body for underlying and supporting the patient's recuperative arm; and a radius and ulna of a generally rectangular shape which is releasably connected to a third distal surfaces of said monolithic humerus support for recuperatively supporting a hand and foreman of a patient.

17. An arm elevation support device a defined in claim 16 wherein said radius and ulna support includes:
an enlarged end portion with at least one hand-receiving member.

18. An arm elevation support device as defined in claim 17 wherein said radius and ulna support comprises:
a substantially rigid backing member affixed to a lateral face of said monolithic member and carrying at least one releasably connecting hook and pile type fastening strip.

19. An arm elevation support device as defined in claim 18 and further comprising:
a first retaining strap releasably connected to said monolithic support and being operable to extend about a humerus of a patient's arm.

20. An arm elevation support device as defined in claim 19 and further comprising:
at least a second retaining strap releasably connected to said radius and ulna support and being operable to extend about the radius and ulna of a patient's arm.

21. An arm elevation support device for recuperative support following rotator cuff surgery, humeral head or shaft fracture correction, or the like comprising:
a generally monolithic humerus support having,
a first proximal surface of said monolithic humerus support concave to be operably received about a patient's rib cage to laterally distribute supporting loads of said arm elevation support device,
a second surface which extends at a substantially forty-five degree angle with respect to said first proximal surface
a third distal surface substantially parallel to said first proximal surface and extending at substantially forty-five degree angle with respect to said second surface, and
a fourth surface substantially normal to said first proximal surface and perpendicular to said third distal surface;
a contoured well shoulder anchor having,
a contoured sleeve portion operable to be worn around the acromial region of a patient's well arm and shoulder and extend in supporting contact about the deltoideus and deltoid regions of a patient's well arm and shoulder,
a first strap connected to an anterior segment of said contoured well shoulder anchor and extending across a patient's upper torso and being connected to an anterior portion of said monolithic humerus support, and
a second strap connected to a posterior segment of said contoured well shoulder anchor and extending across a back portion of a patients's torso and being releasably connected to a posterior portion of said monolithic humerus support wherein the shoulder region of a patient's opposing well arm operably provides support for said generally monolithic humerous support positioned on an opposite side of a patient's body for underlying and supporting the patient's recuperative arm;
radius and ulna support comprising,
a generally rectangular monolithic member which is releasably connected to a third distal surface of said monolithic humerus support for recuperatively supporting a hand and forearm of a patient, and
an enlarged end portion with at least one hand-receiving member;
a first retaining strap releasably connected to said monolithic support and being operable to extend about a humeral region of a patient's arm; and
a second retaining strap releasably connected to said radius and ulna support and being operable to extend about the radius and ulna of a patient's arm.

* * * * *